United States Patent [19]
Dubrow et al.

[11] Patent Number: 5,976,336
[45] Date of Patent: Nov. 2, 1999

[54] MICROFLUIDIC DEVICES INCORPORATING IMPROVED CHANNEL GEOMETRIES

[75] Inventors: Robert S. Dubrow, San Carlos; Colin B. Kennedy, Mill Valley; Luc J. Bousse, Menlo Park, all of Calif.

[73] Assignee: Caliper Technologies Corp., Mountain View, Calif.

[21] Appl. No.: 08/845,754

[22] Filed: Apr. 25, 1997

[51] Int. Cl.[6] .......................... G01N 27/26; G01N 27/447
[52] U.S. Cl. .......................... 204/453; 204/455; 204/604; 204/605; 422/68.1; 422/100; 435/287.2; 435/288.5; 435/6; 436/89; 436/94
[58] Field of Search .......................... 204/451, 453, 204/455, 601, 604, 605; 435/297.2, 288.5, 297.3, 6; 210/198.2, 198.3, 656, 658; 422/68.1, 70, 100, 102; 436/89, 90, 94

[56] References Cited

U.S. PATENT DOCUMENTS

| | | | |
|---|---|---|---|
| 4,077,845 | 3/1978 | Johnson | 435/288.5 |
| 4,908,112 | 3/1990 | Pace | 204/601 X |
| 4,963,498 | 10/1990 | Hillman | 436/69 |
| 5,015,350 | 5/1991 | Wiktorowicz | 204/454 |
| 5,126,022 | 6/1992 | Soane | 204/458 |
| 5,140,161 | 8/1992 | Hillman | 250/341.3 |
| 5,144,139 | 9/1992 | Hillman | 250/341.3 |
| 5,164,598 | 11/1992 | Hillman | 250/341.3 |
| 5,264,101 | 11/1993 | Demorest | 204/452 |
| 5,500,071 | 3/1996 | Kaltenbach | 156/272.8 |
| 5,585,069 | 12/1996 | Zanzucchi | 204/450 X |
| 5,593,838 | 1/1997 | Zanzucchi | 204/450 X |
| 5,603,351 | 2/1997 | Cherukuri | 204/269 X |
| 5,716,825 | 2/1998 | Hancock et al. | 435/287.2 |
| 5,750,015 | 5/1998 | Soane et al. | |
| 5,779,868 | 7/1998 | Parce et al. | 204/601 |
| 5,800,690 | 9/1998 | Chow et al. | 204/601 |

FOREIGN PATENT DOCUMENTS

WO 96/04547   2/1996   WIPO ........................ G01N 27/00
WO 97/02357   1/1997   WIPO ........................ C12P 19/34

OTHER PUBLICATIONS

Effenhauser et al., "Glass Chips for High–Speed Capillary Electrophoresis Separations with Submicrometer Plate Heights," *Anal. Chem.* 65:2637–2642 (1993).

Effenhauser et al., "High Speed Separations of Antisense Oligonucleotides on a Micromachined CE Device," *Anal. Chem.* 66:2949–2953 (1994).

Fan et al, "Micromachining of Capillary Electrophoresis Injectors and Separators on Glass Chips and Evaluation of Flow at Capillary Intersections," *Anal. Chem.* 66:177–184 (1994).

Ghandi, Wiley (1983) Ch. 10 VLSI Fabrication Principles.

Harrison et al., "Micromachining a Miniaturized Capillary Electrophoresis–Based Chemical Analysis System on a Chip," *Science*, 261:895–897 (1993).

Jacobsen et al., "Effects of Injection Schemes and Column Geometry on the Performance of Microchip Electrophresis Devices," *Anal. Chem.* 66:1107–1113 (1994).

Jacobsen et al., "High Speed Separations on a Microchip," *Anal. Chem.* 66:1114–1118 (1994).

Jacobsen et al., "Open Channel Electrochromatography on a Microchip," *Anal. Chem.* 66:2369–2373 (1995).

Jacobsen et al., "Precolumn Reactions with Electrophoretic Analysis Integrated on a Microchip," *Anal. Chem.* 66:4127–4132 (1994).

(List continued on next page.)

*Primary Examiner*—William H. Beisner
*Attorney, Agent, or Firm*—Matthew B. Murphy

[57] ABSTRACT

The present invention generally provides microfluidic devices which incorporate improved channel and reservoir geometries, as well as methods of using these devices in the analysis, preparation, or other manipulation of fluid borne materials, to achieve higher throughputs of such materials through these devices, with lower cost, material and/or space requirements.

81 Claims, 9 Drawing Sheets

OTHER PUBLICATIONS

Jacobsen et al., "Fused Quartz Substrates for Microchip Electrophoresis," *Anal. Chem.* 67:2059–2063 (1995).

Manz et al., "Miniaturized Total Chemical Analysis Systems: A Novel Concept for Chemical Sensing," *Sensor and Actuators* B1:244–248 (1990).

Manz et al., "Micromachining of Monocrystalline Silicon and Glass for Chemical Analysis Systems," *Trends in Anal. Chem.* 10 (5):144–149 (1991).

Manz et al., "Planar Chip Technology for Miniaturization and Integration of Separation Techniques into Monitoring Systems," *J. Chromatog.* 593:253–258 (1992).

Manz et al., "Electroosmotic Pumping and Electrophoretic Separations for Miniaturized Chemical Analysis Systems," *J. Micromech. Microeng.* 4:257–265 (1994).

Ramsey et al., "Microfabricated chemical measurement systems," *Nature Med.* 1 (10):1093 (1995).

Seiler et al., "Planar Glass Chips for Capillary Electrophoresis: Repetetive Sample Injection, Quantitation and Separation Efficiency," *Anal. Chem.* 65:1481–1488 (1994).

Seiler et al., "Electroosmotic Pumping and Valveless Control of Fluid Flow Within a Manifold of Capillaries on a Glass Chip," *Anal. Chem.* 66:3485–3491 (1994).

Woolley et al., "Ultra High Speed Separations on a Microchip," *PNAS* 91:11348–352 (1994)

Woolley et al., "High Speed DNA Genotyping Using Microfabricated Capillary Array Electrophoresis Chips," *Anal. Chem.* 69:22128–2186 (1997).

MICROFLUIDIC DEVICES INCORPORATING IMPROVED CHANNEL GEOMETRIES

BACKGROUND OF THE INVENTION

There has been a growing interest in the development and manufacturing of microscale fluid systems for the acquisition of chemical and biochemical information, in both preparative and analytical capacities. Adaptation of technologies from the electronics industry, such as photolithography, wet chemical etching and the like, to these fluidic systems has helped to fuel this growing interest.

One of the first areas in which microscale fluid systems have been used for chemical or biochemical analysis has been in the area of capillary electrophoresis (CE). CE systems generally employ fused silica capillaries, or more recently, etched channels in planar silica substrates, filled with an appropriate separation matrix or medium. A sample fluid that is to be analyzed is injected at one end of the capillary or channel. Application of a voltage across the capillary then permits the electrophoretic migration of the species within the sample. Differential electrophoretic mobilities of the constituent elements of a sample fluid, e.g., due to their differential net charge or size, permits their separation, identification and analysis. For a general discussion of CE methods, see, e.g., U.S. Pat. No. 5,015,350, to Wiktorowicz, and U.S. Pat. No. 5,192,405 to Petersen et al.

Fabrication of CE systems using planar chip technology has also been discussed. See, e.g., Mathies et al., Proc. Nat'l Acad. Sci. (1994) 91:11348–11352, Jacobsen et al., Anal. Chem. (1994) 66:1114–1118, Effenhauser et al., Anal. Chem. (1994) 66:2949–2953. However, typically, such systems employ a single sample introduction point, e.g., a single well for introducing samples that are to be analyzed in the capillary channel. This requires rinsing and reloading the well prior to each analysis. Further, where one wishes to analyze larger numbers of samples, larger components of each sample, e.g., large nucleic acid fragments, proteins and the like, can build up within the sample loading and separation channels, and/or adsorb to capillary walls, eventually affecting the operation of the system.

It would therefore be desirable to provide microfluidic devices, including CE systems, which permit faster analysis of multiple samples, and do so with minimal and even reduced cost, space and time requirements. The present invention meets these and other needs.

SUMMARY OF THE INVENTION

In a first aspect, the present invention provides a microfluidic system, that comprises a planar substrate having a first surface. An analysis channel and a sample loading channel are disposed in the first surface, whereby the loading channel is in fluid communication and crosses the analysis channel at a first intersection. A plurality of sample sources are also provided in fluid communication with the sample loading channel, whereby at least two of these sample sources are in fluid communication with the loading channel on different sides of the first intersection. First and second waste channels intersect the loading channel at second and third intersections, on different sides of the first intersection. The system also comprises a material direction system for transporting samples from each of the sample sources to the loading channel, and for selectively injecting the samples into the analysis channel.

In a related aspect, the present invention provides a microfluidic system as described above, but comprising a preloading module, which comprises a plurality of sample reservoirs and a waste reservoir, wherein each of the sample reservoirs and the waste reservoir are in fluid communication with the sample loading channel.

The present invention also provides methods for electrophoretically analyzing a sample using the devices and systems described herein, which methods comprise transporting a first sample from the first sample source through the first sample loading channel to the first intersection. A portion of the first sample is then injected into the analysis channel and electrophoreses along the analysis channel. A second sample is then transported from a second sample source through the loading channel to the intersection, whereupon a portion of the second sample is injected into the analysis channel.

In a related aspect, the present invention also provides methods of electrophoretically analyzing a sample, as described above, and incorporating a preloading step. The preloading step is carried out concurrently with the electrophoretic analysis of a first sample. In particular, the second or subsequent sample is transported from the second sample reservoir into the loading channel and then to the waste reservoir. This sample is then injected into the analysis channel as desired.

DETAILED DESCRIPTION OF THE INVENTION

I. General

Figure 1A:
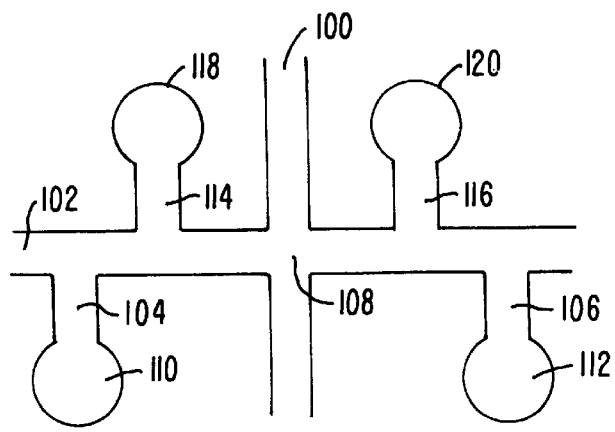
FIGS. 1A–1I schematically illustrates the channel reservoir geometries employed in the devices of the present invention, and their operation in loading and injection of multiple samples (FIGS. 1A through 1E) and in sample preloading (FIGS. 1F through 1I).

The present invention generally provides microfluidic devices which incorporate improved channel and reservoir geometries, as well as methods of using these devices in the analysis, preparation, or other manipulation of fluid borne materials, to achieve higher throughputs of such materials through these devices, with lower cost, material and/or space requirements.

As used herein, the term "microfluidic device or system" generally refers to a device or system which incorporates at least two intersecting channels or fluid conduits, where at least one of the channels has at least one cross sectional dimension in the range of from about 0.1 to about 500 μm, preferably from about 1 to about 100 μm.

The microfluidic devices of the present invention comprise a central body structure in which the various microfluidic elements are disposed. For example, the body structures of the microfluidic devices of the present invention typically employ a solid or semi-solid substrate that is typically planar in structure, i.e., substantially flat or having at least one flat surface. Suitable substrates may be fabricated from any one of a variety of materials, or combinations of materials. Often, substrates are manufactured using solid substrates common in the fields of microfabrication, e.g., silica, silicon or gallium arsenide. In the case of these substrates, common microfabrication techniques, such as photolithographic techniques, wet chemical etching, micromachining, i.e., drilling, milling and the like, may be readily applied in the fabrication of microfluidic devices and substrates. Alternatively, polymeric substrate materials may be used to fabricate the devices of the present invention, including, e.g., polydimethylsiloxanes (PDMS), polymethylmethacrylate (PMMA), polyurethane, polyvinylchloride (PVC), polystyrene, polysulfone, polycarbonate and the like. In the case of such polymeric materials, injection molding or embossing methods may be used to form the substrates having the channel and reservoir geometries as described herein. In such cases, original molds may be fabricated using any of the above described materials and methods.

In the devices described herein, at least one main channel, also termed an analysis channel, is disposed in the surface of the substrate, through which samples are transported and subjected to a particular analysis. Typically, a number of samples are serially transported from their respective sources, and injected into the main channel by placing the sample in a transverse channel that intersects the main channel. This channel is also termed a "sample loading channel." The sample sources are preferably integrated into the device, e.g., as a plurality of wells disposed within the device and in fluid communication with the sample loading channel, e.g., by an intermediate sample channel. However, the devices of the invention may also include sample sources external to the body of the device per se, but still in fluid communication with the sample loading channel.

The sample in the loading channel is drawn or transported across the intersection of the loading channel with the analysis channel. The volume or 'plug' of sample that is disposed within the intersection of these two channels is then drawn down the analysis channel whereupon it is subjected to the desired analysis. The intersection of two channels, e.g., as in the main channel and loading channel, may be a "T" or "three-way" intersection, where the loading channel intersects with and terminates in the main channel, or vice versa. Alternatively, the two channels may intersect and cross each other, creating a "four-way" intersection. In this case, the volume of a sample that is injected is directly related to the volume of the intersection. Where larger volumes of samples are desired, one may generally stagger the intersection of the inlet side of the sample loading channel, e.g., the sample side, and the intersection of the outlet side of the loading channel, e.g., the waste side, whereby more sample is disposed within the analysis channel during loading, e.g., as defined by the length of the analysis channel between the staggered intersections.

For ease of discussion, the devices and systems of the present invention are generally described in terms of the performance of capillary electrophoresis (CE) of a sample. Accordingly, for such operations, the main or analysis channel will generally include a sieving matrix, buffer or medium disposed therein, to optimize the electrophoretic separation of the constituent elements of the sample. However, it will be appreciated upon reading the instant disclosure that the microfluidic devices incorporating the improved geometries described herein are also applicable to a wide variety of non-CE applications, and may be used to perform any of a number of different analytical reactions on a sample, e.g., as described in commonly assigned U.S. patent application Ser. No. 08/761,575, filed Dec. 6, 1996, and U.S. provisional patent application No. 60/086,240, filed Apr. 4, 1997 (Attorney Docket No. 17646-000300), each of which is hereby incorporated herein by reference in its entirety for all purposes.

As noted above, the devices of the present invention employ channel and reservoir geometries that reduce the costs associated with producing the device, by reducing the amount of material required to fabricate the device itself. In addition, the devices of the invention are able to perform analyses with a much higher throughput rate, as well as facilitate those analyses, by: (1) reducing the distance which a particular sample must travel, or be transported, from its origin on the device to the analysis region or channel; (2) increasing the number of samples that may be placed into a single device; (3) allowing one sample to be analyzed while another is being drawn into place, or "preloaded," for subsequent analysis; and (4) providing a common point up to which samples may be preloaded, whereby timing of loading and injection cycles is standardized for all samples.

II. Cost Reduction

In general, in fields employing microfabrication, it is desirable to employ the principles of "shrinking" to optimize the fabrication process. Shrinking generally refers to the optimization of a device at a first scale, followed by the proportional scaling down of the size of the device. Shrinking provides a two-fold advantage in device design and manufacture. First, it provides the readily apparent advantages of reducing the overall product size. Because of this smaller size, the product has smaller space requirements, which can, in turn, be exploited by integrating the device within smaller overall systems. Further, in many cases, microfabricated devices, including, e.g., microprocessors, microfluidic devices, and the like, are fabricated from larger wafers of substrate material, e.g., silicon, silica, etc. As such, by reducing the size of each individual device, one can increase the number of devices which can be produced from a single wafer, reducing the materials costs accordingly.

Furthermore, this increase in the number of devices produced from a single wafer also substantially reduces the number of devices that are lost due to flaws in a wafer. For example, where one produces only four devices from a single substrate wafer, a single, small, critical flaw wholly contained within one device will result in a 25% loss, i.e., 1 of 4 devices will include the flaw. However, where one produces 20 different devices from a single wafer, only 5% of the devices or 1 of 20 will include the flaw. Thus the cost advantages of reducing device size are two-fold.

In the case of the devices of the present invention, dimensions per device will generally range from about a length and width dimensions of from about 5 mm to about 100 mm for a device capable of analyzing multiple samples, however, larger or smaller devices may also be prepared depending upon the number of analyses that are to be performed, and the desired volume of the reagent reservoirs. In preferred aspects, the devices will have length and width dimensions of from about 5 mm to about 50 mm.

The optimized channel and well geometries incorporated into the devices of the present invention allow for a substantially reduced substrate requirement per device. As a result of the reduction in substrate requirements, costs associated with the substrate aspect of the device are substantially reduced as a result of an increase in the number of substrates/wafer and decrease in the percentage of substrates lost/wafer. Although described in terms of silica or silicon based substrate materials, it will be readily appreciated that the cost and material savings provided by the present invention are applicable to a wide range of substrate materials, e.g., glass, polymeric materials, etc.

III. Increased Throughput

As noted previously, the improved channel and reservoir geometries incorporated in the devices of the present invention also allow for substantially improved throughput for performing particular analyses on multiple samples. In particular, in any fluidic system, a substantial amount of time is spent in transporting a material from one location in the system to another. This is particularly the case in capillary electrophoresis systems where transportation of material from one location to another in the system, i.e., from a sample well to the separation capillary, is carried out electrophoretically. This problem is further magnified where the system is used in the serial analysis of multiple different samples.

The channel and reservoir geometries incorporated into the devices and systems of the present invention, on the other hand, result in substantially shorter transit times from a sample reservoir to the analysis portion of the device, e.g., channel. The improved geometries also permit the incorporation of greater numbers of sample reservoirs per unit area of substrate. Additionally, these geometries permit the performance of a 'preloading' operation which allows the analysis of one sample in the analysis region or channel, while another sample is being transported from its reservoir to a location adjacent to the analysis region or channel. The combination of these elements allows for a substantial increase in the throughput of the device.

A. Multiple Sample Wells

In one aspect, the devices and systems of the present invention employ multiple sample sources, wells or reservoirs for a given analysis channel, allowing the serial analysis of multiple samples in a single device merely by sequentially injecting each of the samples from its respective reservoir into the analysis channel, i.e., drawing a sample from a first reservoir and injecting it into the analysis channel, then drawing a sample from a second reservoir and injecting it into the analysis channel. Although generally described herein in terms of sample wells or reservoirs fabricated into the microfluidic device, it will also be understood that such sample reservoirs may also exist externally to the device per se, while remaining in fluid communication with the various points on the device as described herein.

Employment of multiple sample reservoirs provides the advantage of being able to serially analyze multiple samples without having to manually load each sample after the analysis of a previous sample has concluded. The devices of the present invention include at least two separate sample reservoirs on a single substrate and in fluid communication with a given analysis channel. Typically, the devices include at least four separate sample reservoirs, more typically at least six separate sample reservoirs, preferably, at least eight separate sample reservoirs, and more preferably, at least twelve separate sample reservoirs, and often at least 16 separate sample reservoirs for a given analysis channel. Each of the sample wells is typically in fluid communication with a sample loading channel which intersects and is in fluid communication with the analysis channel. A load/waste reservoir is typically supplied in fluid communication with the sample loading channel on the opposite side of the intersection of the loading channel with the analysis channel. This allows a sample to be loaded by drawing the sample across the intersection and toward the load/waste reservoir. An additional preload channel and reservoir is provided in fluid communication with the sample loading channel on the same side as the samples to be loaded, to permit preloading of one sample while a previous sample is being transported along the main channel, e.g., by flowing the sample from its own well to the load/waste well on the same side of the intersection and thus, not crossing the intersection.

In preferred aspects, the multiple sample reservoirs are disposed at locations on the substrate on both sides of the analysis channel. By locating the sample reservoirs on both sides of the analysis channel, one can minimize the distance, and thus the channel length, between any given reservoir and the point on the analysis channel at which the sample is to be injected into that channel, by clustering the sample reservoirs around the point at which the samples will be injected into the analysis channel. By minimizing the length of the channel between the sample reservoirs and the analysis channel, one minimizes the transit time for transporting a sample from its reservoir to the analysis channel. In addition, one also minimizes any effects that result during the transportation of the fluids, e.g., adherence of components to the device, electrical effects in electroosmotic (E/O), or electrophoretic systems, which effects may not be desirable prior to injection in the analysis channel, e.g., electrophoretic biasing or separation of sample components.

In particularly preferred aspects, the sample reservoirs are equally allocated on both sides of the analysis channel. Thus, in these preferred aspects, the device will include at least two, typically at least three, preferably at least four, more preferably, at least six, and still more preferably at least eight separate sample reservoirs on each side of the analysis channel.

As noted previously, injection of a sample into the main analysis channel typically involves drawing the sample across the intersection of the loading channel and the analysis channel. Accordingly, in preferred aspects, the devices and systems of the present invention will typically include a load/waste reservoir and channel in fluid communication with the sample loading channel on the opposite side of the analysis channel from the sample that is to be loaded. Application of a voltage gradient between the desired sample reservoir and the load waste/reservoir on the opposite side of the analysis channel then causes material transport through the sample loading channel and across the intersection of the loading channel and the analysis channel (also termed the injection point) and into the load/waste channel and reservoir.

Because the devices and systems of the present invention preferably include samples located on each side of the analysis channel, such devices will also include a load/waste reservoir and corresponding channel on each side of the analysis channel and in fluid communication with the sample loading channel. Specifically, the preloading well for samples on one side of the analysis channel is the load/waste reservoir for the samples on the other side of the channel. A schematic illustration of this feature is illustrated in FIG. 1.

In brief, FIG. 1A schematically illustrates an intersection between two channels in a microfluidic device (not shown), e.g., a main analysis channel 100 and a sample loading channel 102. Sample loading channel also includes first and second sample introduction channels 104 and 106, respectively, in fluid communication with the sample loading channel on opposite sides of the intersection 108, and which sample introduction channels are also in fluid communication with first and second sample sources 110 and 112, respectively, e.g., a sample reservoir disposed in the device. In addition to the first and second sample channels, the sample loading channel on each side of the intersection is also in fluid communication with first and second load/waste channels 114 and 116, respectively, which are in turn, in fluid communication with first and second load/waste reservoirs 118 and 120, respectively.

Figure 1B:
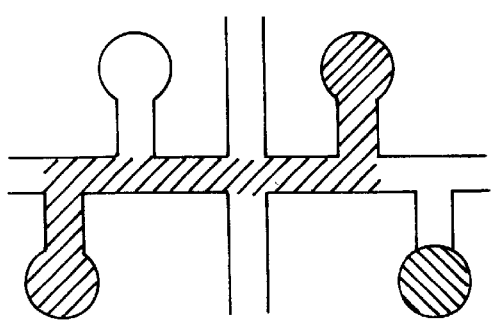
Figure 1C:
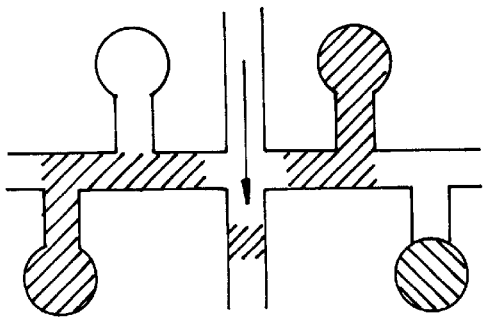

FIGS. 1B through 1E schematically illustrate the sequential injection of a sample from each of the first and second sample wells. In particular, FIGS. 1B and 1C show the first sample (indicated by hatching ////) being drawn into the sample loading channel 102 and across the intersection 108 of the loading channel with the main channel 100, and into the second load/waste channel 116. In electrical material direction systems, e.g., E/O flow or electrophoretic transport systems as generally described herein, this is accomplished by applying a voltage at the first sample reservoir 110 and the second load/waste reservoir 120, to achieve material movement along the path of current flow. The plug of sample material at the intersection is then injected into the main channel 100, by applying a voltage at points on the main channel on opposite sides of the intersection 108, i.e., buffer and waste reservoirs located at the termini of the main channel 100. During injection, the voltage applied at sample reservoir 110 and second load/waste reservoir 120 may be removed, e.g., allowing these reservoirs to 'float.' However, typically a voltage will be maintained at these reservoirs, so as to achieve a net material flow away from the intersection, e.g., pulling the sample away from the intersection, to avoid any diffusion or leaking of the sample into the intersection during analysis.

Figure 1D:
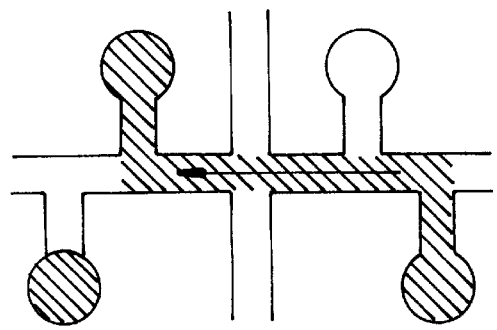
Figure 1E:
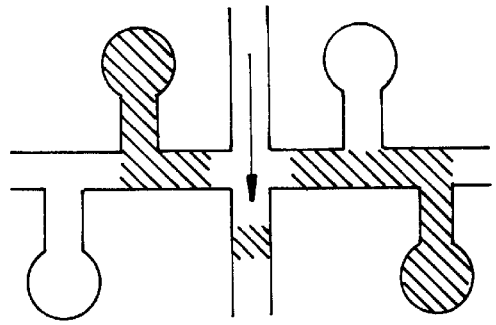
Figure 1G:
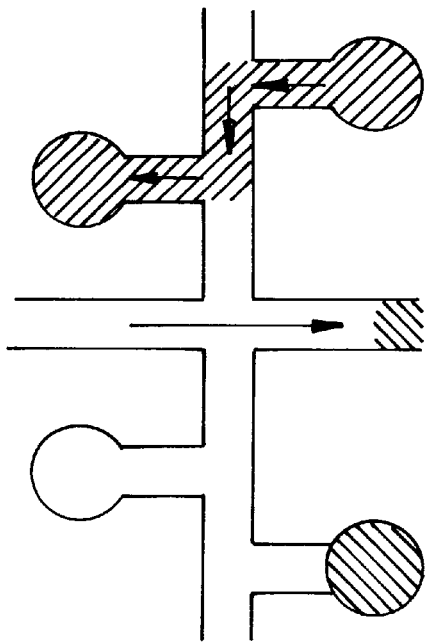

The second sample (indicated by reverse hatching \\\\) is loaded and injected into the main channel 100, in the same fashion as the first, as shown in FIGS. 1D and 1E, except that during loading, the voltages are applied at the second sample reservoir 112 and the first load/waste well 118.

In addition to allowing injection into the analysis channel of samples from both sides of the analysis channel, and in contrast to devices lacking this feature, incorporation of load/waste reservoirs on both sides of the analysis channel also permits one sample to be preloaded while another sample is being analyzed in the analysis channel, as noted above.

For example, in typical planar chip based CE devices incorporating a separation channel and a loading channel in a cross-channel structure, a sample is loaded into the separation channel by placing it in a reservoir at the terminus of the loading channel and applying a voltage across the loading channel until the sample has electrophoresed across the intersection of loading channel and the separation channel. Typically, the application of voltage is via an electrode disposed within the reservoir or well at the terminus of the given channel (also termed a "port"). The plug of material at the intersection is then electrophoresed down the separation channel by applying a voltage across the separation channel. In order to avoid disrupting the separation of the sample, i.e., by interrupting the electric field, one must wait until that separation has concluded prior to loading a subsequent sample.

In the channel structures described herein, however, while a first sample is being analyzed in the analysis channel, e.g., by electrophoresis, a subsequent sample may be transported to a location in the loading channel closer or even adjacent to the injection point. In particular, by applying an appropriate voltage across the sample reservoir and the load/waste reservoir that is in fluid communication with the sample loading channel on the same side of the analysis channel, the sample is transported from its respective reservoir through a portion of the sample loading channel and to that load/waste channel/reservoir, without crossing the analysis channel. Further, by maintaining the voltages applied in this preloading procedure at levels such that the voltage at the preloading point, e.g., the intersection between load/waste channel 114 and loading channel 102, is substantially equal to that at the injection point (108), one can carry out this preloading without affecting the transportation of material within the analysis channel, e.g., without producing transverse electric fields between the loading channel and the analysis channel. Where one is determining this voltage at a given intermediate point in a channel ($V_i$), which has a first voltage applied at one end $V_a$ and a second voltage applied at the other end $V_b$, determination of the intermediate voltage is as follows:

$$V_i = V_b + \frac{R_b(V_a - V_b)}{R_a + R_b}$$

Where $R_a$ is the resistance between the point at which $V_a$ is applied and the intermediate point at which $V_i$ is to be determined and $R_b$ is the resistance between the point at which $V_b$ is applied and the intermediate point where $V_I$ is to be determined.

Upon completion of analysis of the previous sample, the subsequent sample, already within the sample loading channel, is then merely transported across the intersection of the loading channel and the analysis channel, and the plug of sample material at the intersection is then drawn down the analysis channel, as before.

Figure 1I:
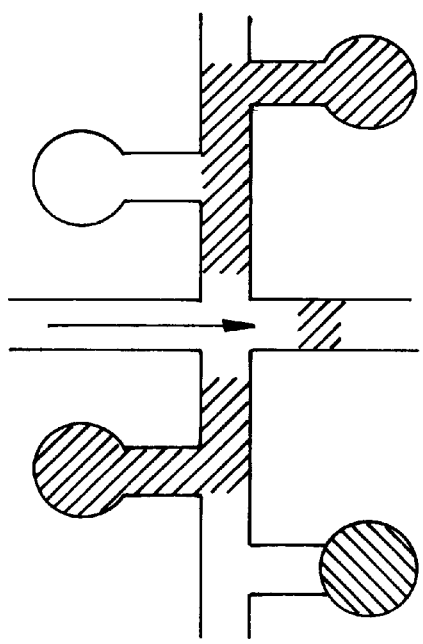
Figure 1F:
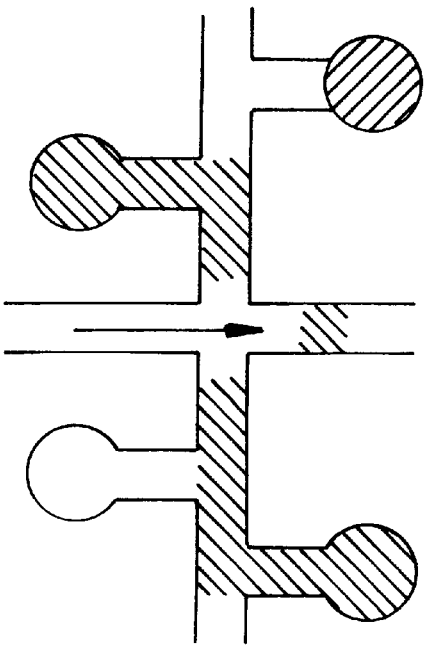
Figure 1H:
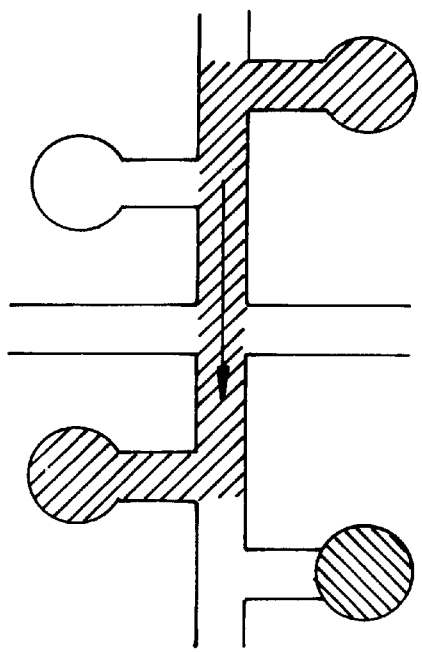

FIGS. 1F through 1I illustrate the same channel intersection structure shown in FIGS. 1B through 1E, but wherein that structure is used to preload one sample while a previous sample is being analyzed along the main channel. In particular, FIG. 1F illustrates the post injection of the first sample, e.g., as described in FIGS. 1B through 1E, above. While the first sample is being analyzed, the second sample is transported into a position in the sample loading channel closer to the injection point, intersection 108, by moving the second sample into the sample loading channel and into the second load/waste channel. As shown in FIG. 1H, following the completion of the analysis of the first sample, e.g., electrophoretic separation, etc., the second sample is loaded into the analysis channel by drawing it across the intersection 108, and injecting it into the analysis channel (FIG. 1I). This process is then repeated for all the samples that are to be analyzed.

Figure 2A:
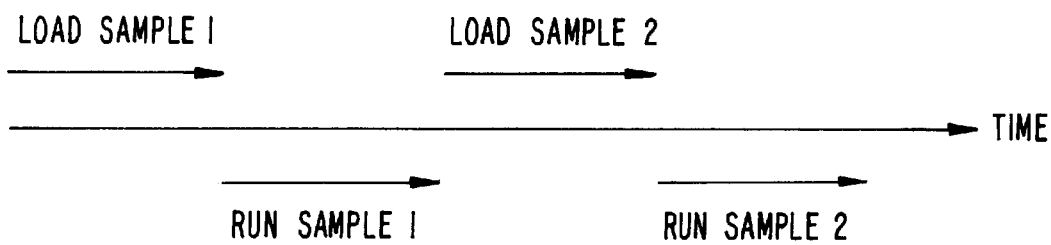
FIG. 2 is a schematic illustration of the chronology of the various material transport steps involved in performing capillary electrophoresis in a microfluidic device of the present invention (bottom) as compared to prior art CE systems lacking a preloading feature (top).
Figure 2B:
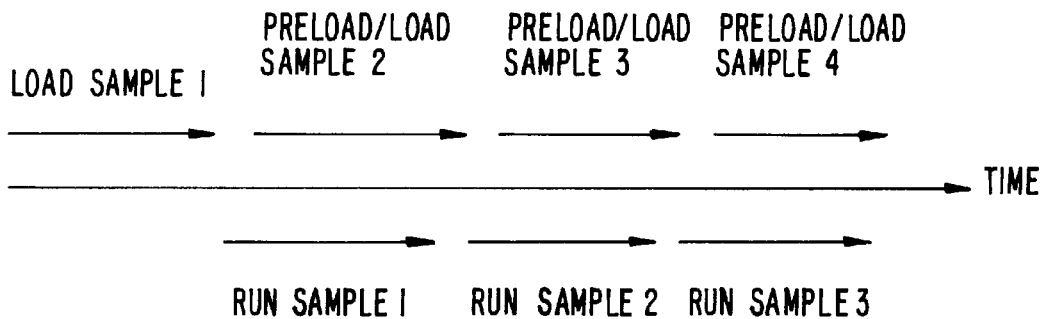

FIG. 2 schematically illustrates the substantial time savings derived from sample preloading using the devices incorporating this preloading feature over devices not incorporating this feature. Briefly, Panel A schematically illustrates the timing of events required to load and inject multiple samples into the analysis channel using a typical microfluidic device, i.e., which does not include a separate load/waste reservoir on each side of the analysis channel. In particular, loading any given sample requires the transportation of the sample across the intersection of the analysis channel and the loading channel, followed by the transportation of the sample plug at the intersection down the separation channel. In these typical devices, no samples are loaded while a given sample is being analyzed, as this would result in the disturbance of the material flow in the analysis channel. Thus, analysis of one sample must be effectively completed prior to loading a subsequent sample, resulting in a sample loading and injection timeline where loading and analysis of samples does not overlap, as indicated by the arrows.

Panel B of FIG. 2 provides a similar timeline for samples serially analyzed in a device of the present invention, which incorporates an additional load/waste reservoir on the same side as the reservoirs containing the samples to be loaded. Incorporation of this additional load/waste reservoir allows the transporting of a sample from its respective reservoir into the loading channel, without affecting the material flow within the analysis channel, also termed "preloading." As such, while one sample is being transported along the analysis channel, a subsequent sample may be preloaded into the loading channel. As shown, the time savings can be substantial, particularly where multiple samples (e.g., 8, 10, 12, 16 or greater) are being analyzed.

In order to reduce the amount of dead volume between a preloaded sample and the analysis channel, it is generally desirable for the load/waste channel to intersect the sample loading channel at a point that is relatively close to the intersection of the loading channel and the analysis channel. In the microfluidic devices of the present invention, the distance between these two intersections is typically less than 5 mm, preferably less than 2 mm, more preferably less than 1 mm, and often, less than 0.5 mm.

In addition, for multiple sample reservoir devices, it is generally desirable to be able to preload each sample to the same point in the sample loading channel. This permits the standardization and simplification of timing for preloading, loading and injecting each sample. In addition, during this preloading time, a myriad of other operations may be performed on the sample, including dilution, combination with substrates or other reactants, and the like. As such, it is generally preferable for the load/waste channel to intersect the sample loading channel at a point between all of the sample reservoirs and the main channel. Thus, in preferred aspects, each load waste channel intersects the sample loading channel at a point between: (1) the intersection of the sample loading channel and the main channel, and (2) the intersection of the sample loading channel with each of the sample channels. Sample loading and preloading in these devices is described in greater detail below.

Finally, in addition to the above described advantages, the incorporation of multiple sample sources, each having a separate path, at least in part, to the injection point, provides at least one additional advantage, particularly when that system is applied in CE applications. Typical CE systems introduce each sample that is being analyzed by identical paths, e.g., through the same sample well or via the same channel or passage. Often times, this can result in an accumulation within that path of extremely slowly migrating material, e.g., very large nucleic acid molecules or complexes, proteins etc., which accumulation can result in a general fouling of the separation channel or capillary.

By including a separate introduction path for each separate sample that is being analyzed, i.e., as provided herein, as opposed to introducing multiple samples through the same path, such slow migrating material will generally be retained within the sample source or the channel that connects that source to the common sample loading channel. This effect is particularly evident in CE applications which include a sieving matrix or medium within the various channels of the device, which matrix accentuates the differential migration rates of these larger species.

IV. Device Description

Figure 3:
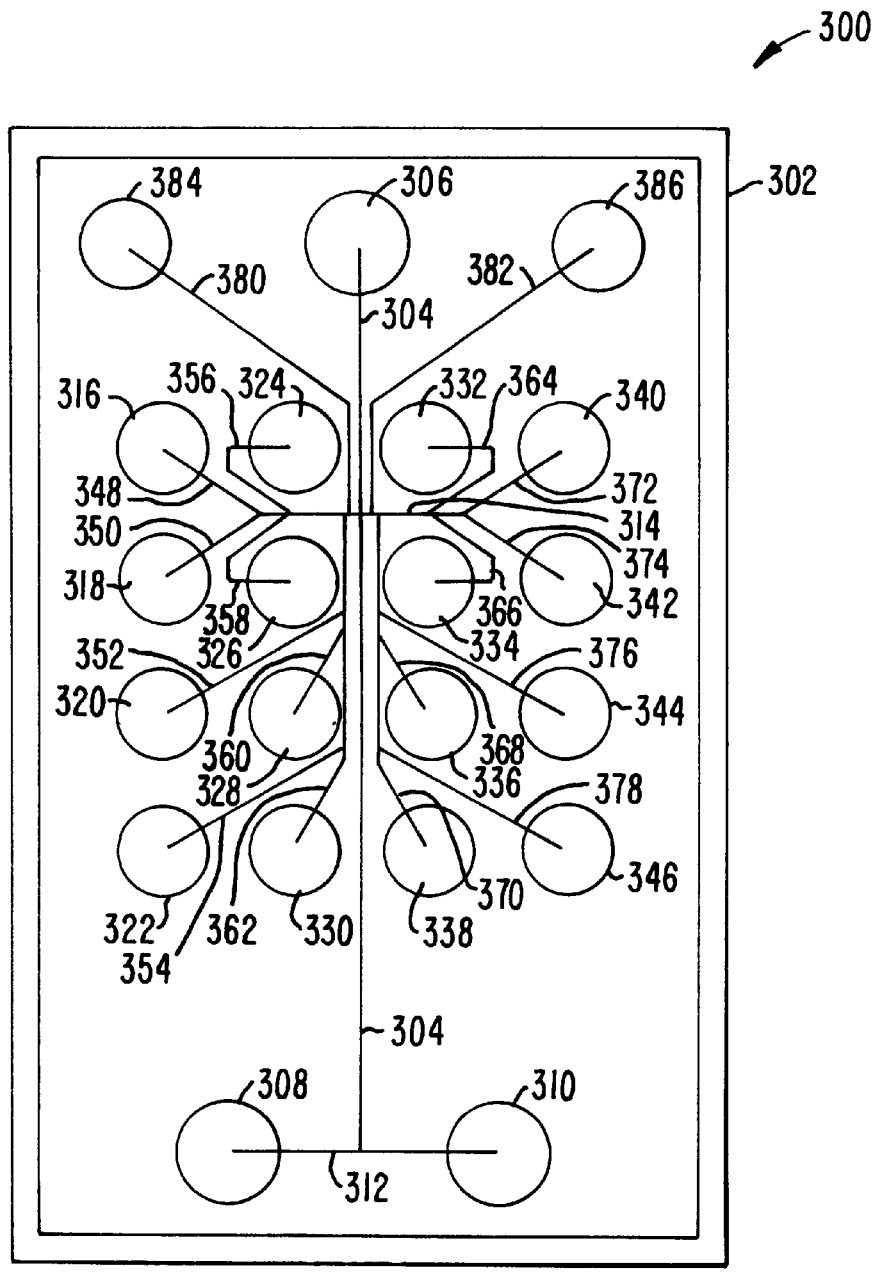
FIG. 3 illustrates one embodiment of a microfluidic device incorporating an improved channel/sample well geometry for performing serial analysis of multiple samples.

An example of a device employing improved channel and reservoir geometries according to the present invention is shown in FIG. 3. As shown, the device 300 is fabricated from a planar substrate 302, which has the various channels fabricated into its surface. A second planar layer overlays the first and includes holes disposed through it to form the various reservoirs. This second planar element is then bonded to the first.

As shown, the device includes a main separation or analysis channel 304 which runs longitudinally down the central portion of the substrate. The main channel 304 originates in and is in fluid communication with buffer reservoir 306, and terminates, and is in fluid communication with waste reservoirs 308 and 310, via waste channel 312. Sample loading channel 314 intersects and is in fluid communication with main channel 304. As shown, the device also includes multiple separate sample reservoirs 316 through 346, inclusive, each of which is in fluid communication with sample loading channel 314, either directly via its respective sample channels 348–378, or via an intermediate sample channel. Load/waste channels 380 and 382 are also provided, in fluid communication with sample loading channel 314, on opposite sides of the intersection of the sample loading channel with main channel 304, and between that intersection and the sample channels on their respective sides of that intersection. Each of these load/waste channels terminates in one of load/waste reservoirs 384 and 386, respectively.

The multiple separate sample reservoirs are disposed on both sides of the main channel, in order to maximize the number of reservoirs that will fit on the substrate, while minimizing the distance that a sample must travel to reach the analysis channel.

In order to control and direct the electrophoretic movement of materials within the device, an electrode is placed into electrical contact with each of reservoirs 306–310, 316–346, 384 and 386. Again, although the present example is described in terms of electrophoretic transport and direction of materials in the device, it will be readily appreciated that other forms of material transport and direction are also envisioned and would be equally benefitted by the present invention, e.g., electroosmotic fluid transport and direction, pressure or pneumatically driven fluid transport systems, including those utilizing micropumps, or other displacement driven systems.

In operation, a first sample is disposed within a sample reservoir, e.g., reservoir 316. The sample is transported along sample channel 348 to loading channel 314, across the intersection of loading channel 314 and main channel 304, by application of an appropriate voltage at sample reservoir 316 and waste reservoir 386. In preferred aspects, appropriate voltages are also applied at buffer reservoir 306 and waste reservoirs 308 and 310, to apply a constraining flow of fluid from the main channel to "pinch" the flow of the sample across the intersection, thereby preventing leakage or diffusion of sample at the intersection. Pinched loading is described in detail in Published PCT Application No. WO 96/04547 to Ramsey et al., which is incorporated herein by reference in its entirety for all purposes.

The sample plug, e.g., the pinched plug, at the intersection of loading channel 314 and main channel 304 is then drawn down main channel 304, by applying a voltage between buffer reservoir 306 and waste reservoirs 308 and 310, while reservoirs 316 and 386 are allowed to float. In some cases, appropriate voltages may be applied to these floating reservoirs in order to draw the sample in the loading channel away from the intersection, so as to avoid the leaking of a sample into the analysis channel.

While the first sample is being transported along main channel 304 and being subject to the analysis of interest, e.g., electrophoretic separation, a second sample may be "preloaded" into position in loading channel 314 for subsequent analysis. This subsequent sample is preloaded from sample reservoir 318 into loading channel 314 and out through load/waste channel 380 to load/waste reservoir 384, by applying an appropriate voltage at sample reservoir 318 and load/waste reservoir 384. As stated previously, the voltages applied at these reservoirs are typically maintained at levels such that the voltage at the injection point (intersection of channels 304 and 314) is substantially equal to the voltage at the preload point (intersection of channel 314 and 382), so as to avoid the generation of transverse fields, i.e., a voltage gradient, between the loading channel and the main channel during the preloading procedure.

Once the first sample has been run down the main analysis channel 304, the preloaded sample in the loading channel 314 is injected across the intersection of the loading channel 314 and the main channel 304 by applying a voltage across sample reservoir 318 and load/waste reservoir 386. The sample plug at the intersection is then transported along main channel 304 by again applying an appropriate voltage across the main channel, while a third sample is preloaded as described above. This is repeated for each sample reservoir on each side of the main channel. Thus, as shown, each side of the main channel includes a separate "preloading module" that includes the collection of sample reservoirs and channels, in fluid communication with a sample loading channel. Each preloading module includes its own load/waste reservoir and channel in fluid communication with the sample loading channel, whereby a sample can be transported from its respective reservoir into the loading channel and to a position in the loading channel that is proximal to the intersection of the loading channel and the main channel, without affecting the movement of material in the main channel. As noted previously, in order to minimize dead volumes between the preloading of a sample and the injection of that sample, it is generally preferred that the load/waste channel for a preloading module, e.g., load/waste channel 380, intersect its loading channel, e.g., 314, at a point close to the intersection of the loading channel and the main channel.

Figure 4:
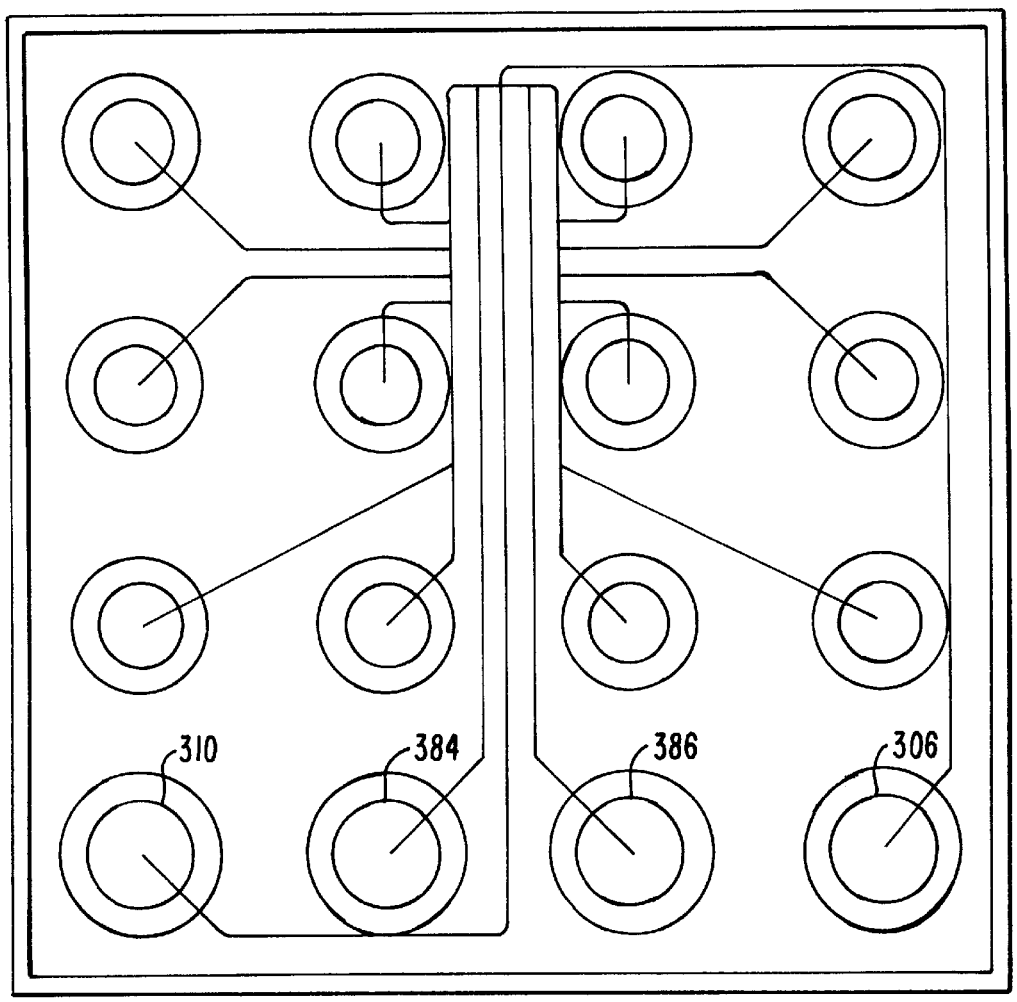
FIG. 4 illustrates another embodiment of a microfluidic device incorporating an improved channel/sample well geometry for performing serial analysis of multiple samples.

A similar channel/reservoir geometry is illustrated in FIG. 4, for a device which includes 12 separate sample reservoirs, as well as the preloading features described above. In order to achieve a more compact geometry, the buffer reservoir 306, waste reservoir 310 and load/waste reservoirs 384 and 386 are located in a row at the bottom of the device. This results in a gridded array of sample/waste/buffer reservoirs, wherein a twelve sample device only occupies approximately one half of the substrate area required for the device shown in FIG. 3. Although this device includes fewer sample reservoirs than the device illustrated in FIG. 3 and described above, the sample:area ratio is substantially increased by optimizing the channel and reservoir geometry. In particular, where the device shown in FIG. 3 has side dimensions of 17.5 mm, one can obtain 49 separate devices from a single 5"5" square substrate plate or wafer, permitting analysis of 588 samples per plate. Assuming the device shown in FIG. 3 is 22.4 mm×37 mm, one can only obtain 15 separate devices or 240 assays per substrate plate.

As noted previously, the devices, systems and methods of the present invention are not limited in application to capillary electrophoresis applications, but may be broadly applied to the field of microfluidics, including fluidic systems employing a variety of material transport mechanisms, including, e.g., electroosmotic transport systems, electrophoretic transport systems and even pressure driven systems. However, where these devices, systems and methods are used in capillary electrophoresis applications, i.e., to separate sample components, e.g., nucleic acid fragments, it is generally desirable to reduce the level of electroosmotic flow within the channels of the device, thereby optimizing the differential mobility of differentially charged or sized species within the system, and thus their separability.

Accordingly, in preferred aspects, where the devices and systems of the invention are employed in capillary electrophoresis applications, the channels of the device are pretreated with a dynamic sieving matrix. Such dynamic sieving matrices typically comprise charged polymers, e.g., linear polyacrylamide polymers, which are capable of binding the walls of the capillary channels, thereby shielding the charged surfaces of these walls, and reducing electroosmotic flow. Examples of particularly preferred dynamic sieving matrices include those discussed in U.S. Pat. No. 5,264,101, incorporated herein by reference in its entirety for all purposes, as well as the GeneScan™ sieving buffers available from Perkin Elmer Corp.

The invention is further described with reference to the following nonlimiting examples.

EXAMPLES

Example 1

Multisample Analysis

A 16 sample capacity device, or LabChip™ having the geometry shown in FIG. 3 was fabricated from a 100 mm diameter white crown glass wafer having a thickness of 500 μm. A wafer was used for its compatibility with most commercially available photolithography equipment. Channels 75 μm wide and 12 μm deep, and having the configuration shown, were etched in the glass substrate using standard photolithographic techniques. Holes were drilled through a separate piece of glass 5 inches on a side, whereby the holes corresponded to the termini of the various channels. The two pieces of glass were thermally bonded to form the channel and well structure shown. The device having dimensions of 22.4 mm×37 mm was cut from the larger material.

Sieving buffer was prepared by weighing 2.5 grams GeneScan Polymer (Perkin Elmer Corp.), 0.5 g of Genetic Analysis Buffer (Perkin Elmer Corp.) and 2.5 ml water into a 20 ml scintillation vial, which was then vortexed for 30 seconds. One μl of Syber Green 1 DNA intercalation dye (Molecular Probes Inc.) was added to 0.5 ml of the sieving buffer which was again vortexed for 30 seconds in a 1.5 ml Eppendorf tube. Five μl PCR Marker (Promega Corp.) containing 6 DNA fragments ranging in size from 50 to 1000 bp was mixed with 15 μl of the buffer containing the Syber Green and vortexed.

The channels in the LabChip™ were filled with 3.5% GeneScan™ buffer (Perkin-Elmer Corp.) by applying 5 μl to the buffer well and then applying slight pressure with a syringe for 5 seconds on the well. This buffer contains a polymer which retards the migration of DNA relative to its size and also modifies the walls of the channel to reduce electroosmotic flow. Four μl of the GeneScan buffer was then added to the buffer and waste wells.

A DNA standard, PhiX174 cleaved with HinfI (Promega Corp.), was diluted 50:1 in 3.5% GeneScan™ buffer containing 1 μM SyberGreen DNA intercalating dye (Molecular Probes, Inc.) and 4 μl of this solution was added to each of the 16 sample wells. The device was then placed under a Nikon inverted Microscope Diaphot 200, with a PTI Model 814 PMT detection system, for epifluorescent detection. An Opti-Quip 1200–1500 50 W tungsten/halogen lamp coupled through a 40×microscope objective provided the light source. Excitation and emission wavelengths were selected with a FITC filter cube (Chroma, Brattleboro Vt.) fitted with appropriate filters/dichroic mirrors. Reagent well currents and voltages on the chip were controlled using a voltage controller having a separate controllable electrode for each of the separate reservoirs on the microfluidic device. The serial injection of samples proceeded along the following cycle:

Step 1: Initial Sample Preload (45 secs.)
Step 2: Sample Load (5 secs.)
Step 3: Inject (1 sec.)
Step 4: Pull Back (2 secs.)
Step 5: Run/Next Sample preload (85 secs.)
Step 6: Next Sample Load (5 secs.)
Step 7: Repeat Steps 3–6

An example of the cycle of currents applied at the various reservoirs during a single cycle is provided in the following table.

The sample pull back step was inserted to pull the sample away from the intersection of the loading channel with the main channel, and thus prevent bleeding over of the sample. Also, during the loading steps, e.g., steps 2 and 6, a pinching flow was delivered to the intersection such that the flow of sample would not diffuse into the main channel as a result of convective effects. Applied voltages were controlled using a current based control system, e.g., as described in commonly assigned U.S. patent application Ser. No. 08/678, 436, filed Jul. 3, 1996, and incorporated herein by reference in its entirety for all purposes. Currents applied for each of the above steps were as shown in Table 1, below. The voltage applied to main buffer reservoir 306 was controlled at a level at which it provided an appropriate balancing current in the remainder of the system:

| Step | Sample Well | Sample Current (μA) | Load/Waste Well | Load/Waste Current (μA) | Buffer Well | Waste Current (μA) |
|---|---|---|---|---|---|---|
| 1 | 332 | −7 | 386 | 10 | 310 | −2 |
| 2 | 332 | −7 | 384 | 10 | 310 | −2 |
| 3 | 332 | 5 | 384 | 5 | 308 | −12 |
| 4 | 332 | 1 | 384 | 1 | 308 | −8 |
| 5 | 334 | −7 | 386 | 10 | 308 | −7.5 |
| 6 | 334 | −7 | 384 | 10 | 310 | −2 |

Figure 5:
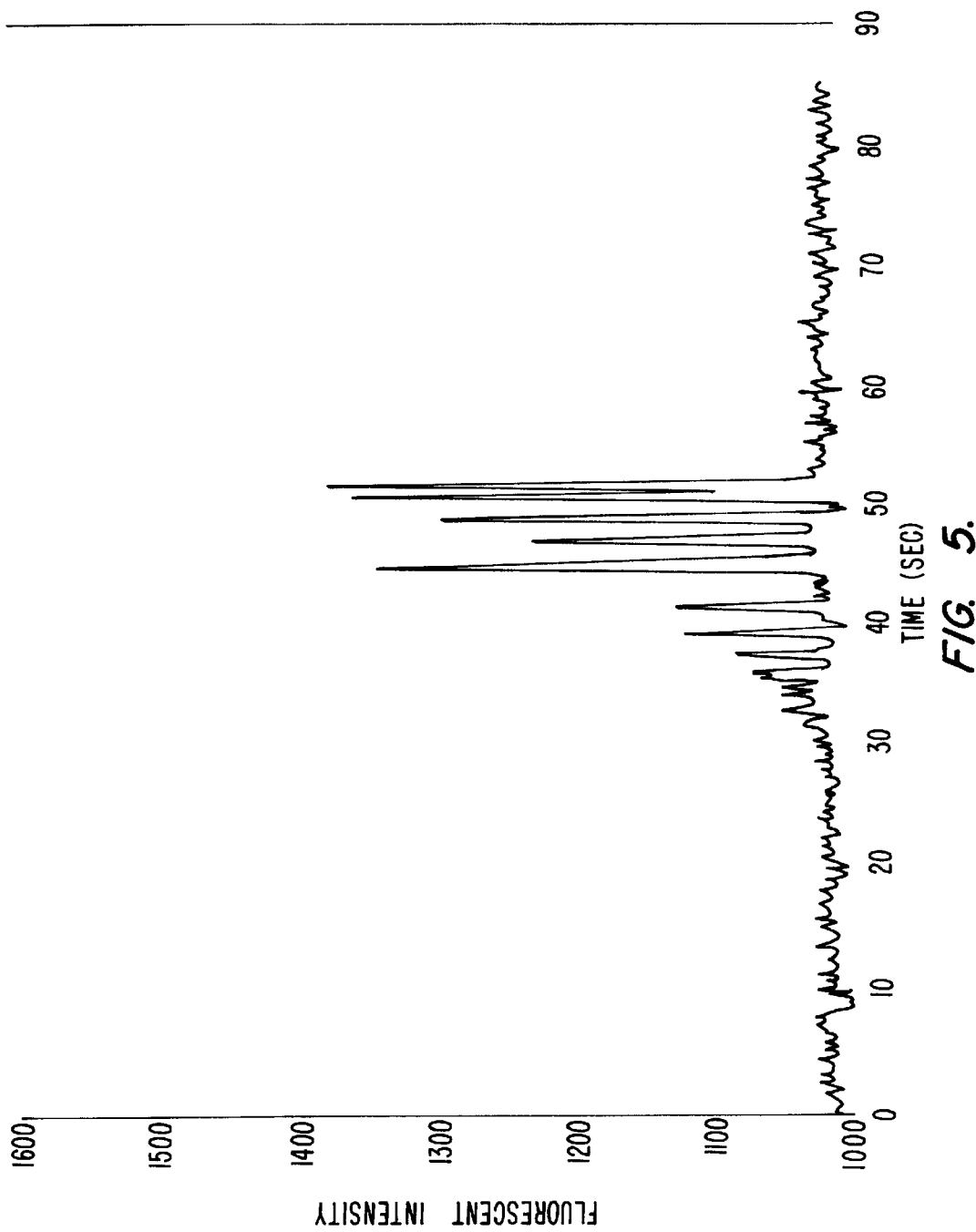
FIG. 5 is a plot of retention times for fluorescently dyed nucleic acid fragments injected into a CE channel fabricated into a substrate employing the improved channel/sample well geometry of the present invention.

The results of the first separation using this method are shown in FIG. 5. As is clear from this figure, this method of performing capillary electrophoresis yields high resolution in a substantially reduced time-frame. Further, no degradation of resolution was seen through separation of all 16 samples.

Example 2

Determination of Cross Contamination Levels for Successive Samples

In order to ascertain whether successive runs in the device experienced any cross contamination of samples, two different nucleic acid fragment samples and a plain buffer sample were run in succession and examined for contaminating effects.

Each well of the 16 well device described above, was loaded with either the PCR Marker, the PhiX174 cleaved with HAEIII or plain buffer. The wells were loaded such that they would be injected successively in this order. The fluorescence data for each run was plotted as a function of time.

Figure 6A:
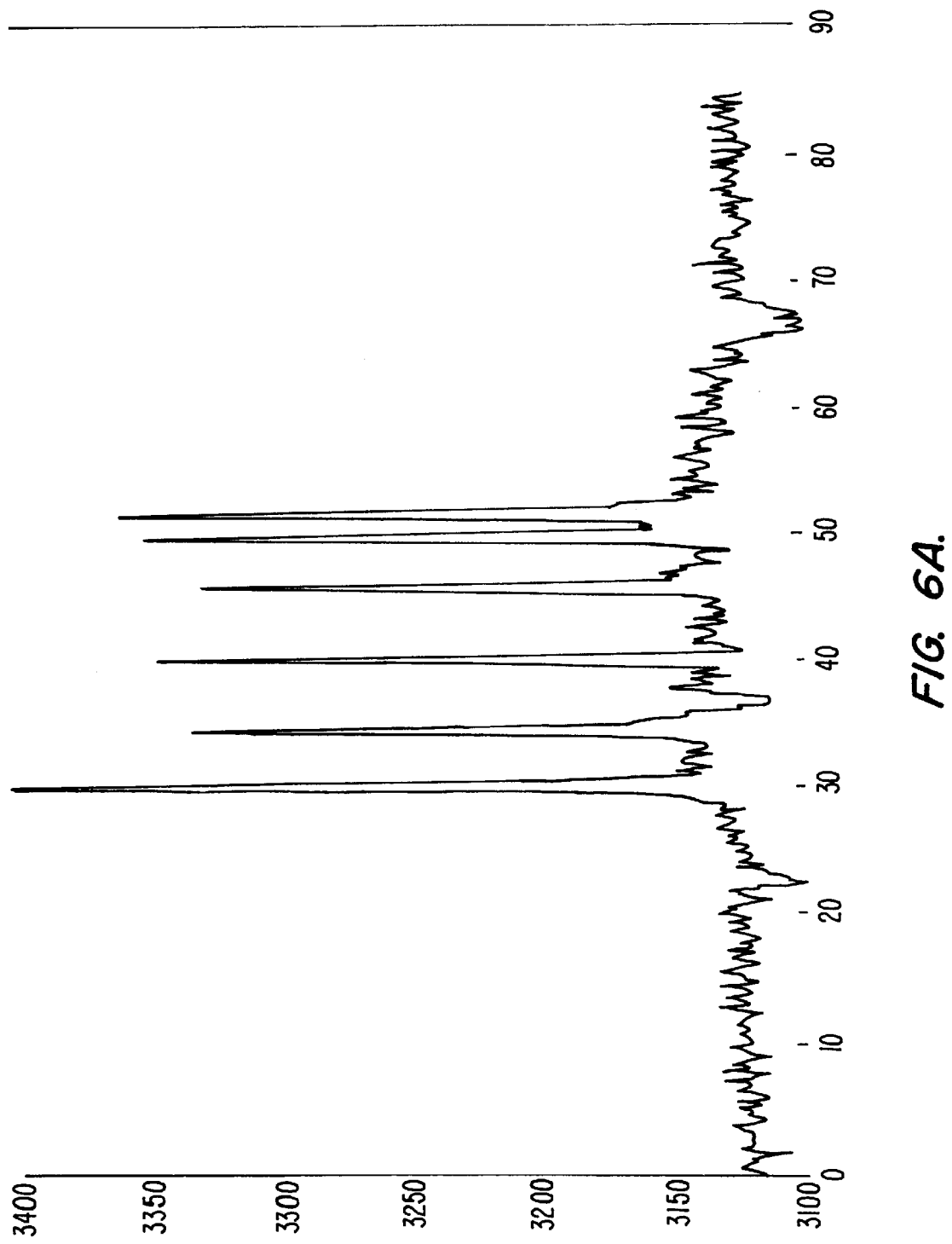
FIGS. 6A–6C are plots of fluorescence vs. time for a set of PCR fragments intercalated with a fluorescent dye (FIG. 6A), PhiX174 DNA, cleaved with HaeIII and intercalated with a fluorescent dye (FIG. 6B) and a buffer blank, serially injected into the analysis channel of a microfluidic device incorporating the channel/sample well geometry of the present invention.
Figure 6B:
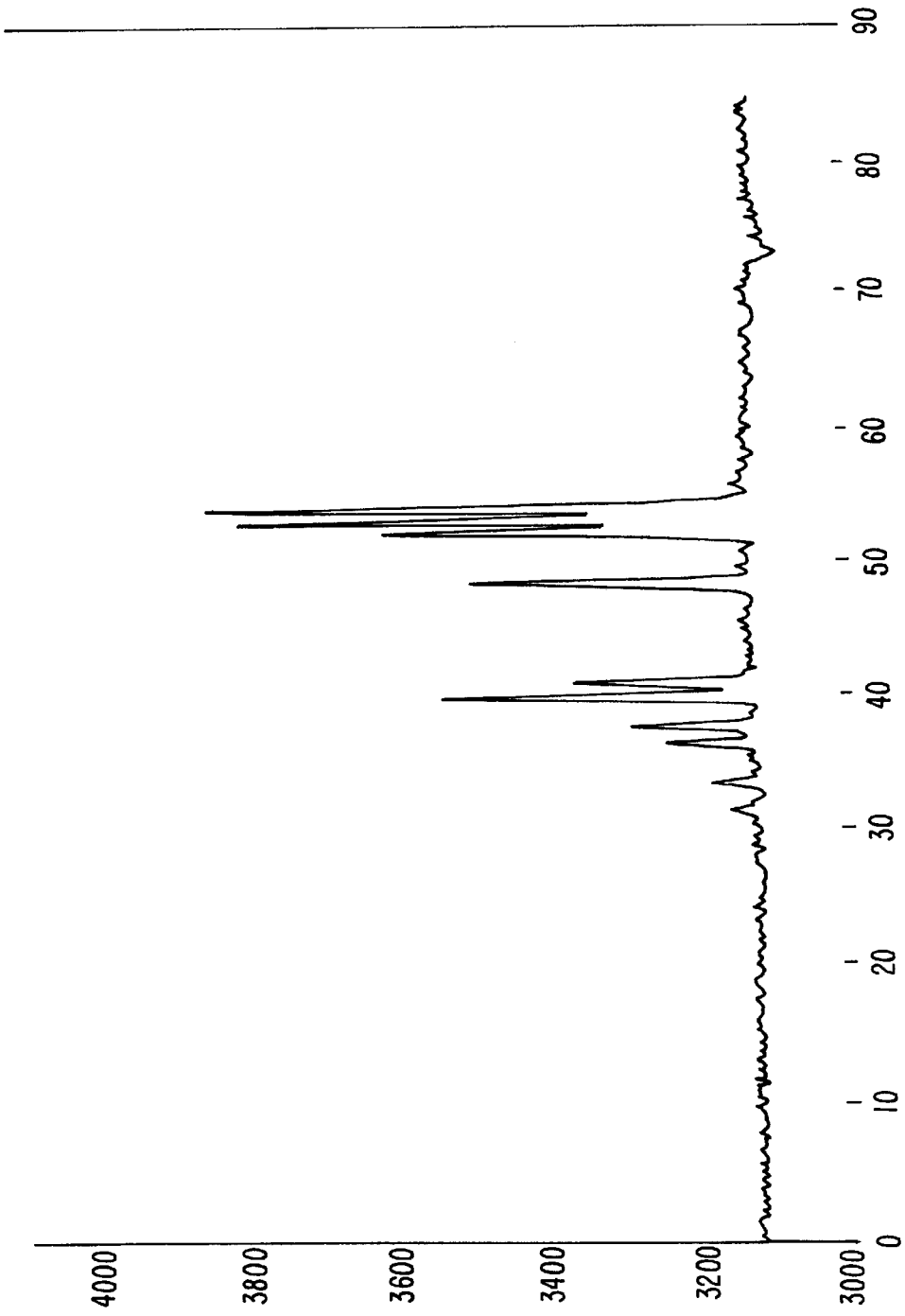
Figure 6C:

FIGS. 6A, 6B and 6C show plots of successive injections of PCR Marker, PhiX174/HaeIII and buffer blanks. FIG. 6B illustrates that no spurious fluorescence peaks are detectable bleeding over from the previous PCR Marker run, into the PhiX174/HaeIII run. Further, FIG. 6C shows that even in a plain buffer run, there are no detectable levels of cross contamination from the prior DNA containing samples.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

We claim:

1. A microfluidic system, comprising:
   a planar substrate having a first surface;
   an analysis channel disposed in said substrate;
   a sample loading channel disposed in said substrate and in fluid communication and crossing said analysis channel at a first intersection;
   a plurality of separate sample sources in fluid communication with said sample loading channel, whereby there is at least one of said plurality of separate sample sources in fluid communication with said sample loading channel on each side of said first intersection; and
   first and second load/waste channels disposed in said substrate, each of said first and second load/waste channels intersecting said sample loading channel at second and third intersections, respectively, said second and third intersections being on different sides of said first intersection.

2. The microfluidic system of claim 1, wherein said second and third intersections are each within 5 mm of said first intersection.

3. The microfluidic system of claim 1, wherein said second and third intersections are each within 2 mm of said first intersection.

4. The microfluidic system of claim 1, wherein said second and third intersections are each within 1 mm of said first intersection.

5. The microfluidic system of claim 1, wherein there are at least two sample sources in fluid communication with said sample loading channel on the same side of said first intersection, and said first load/waste channel intersects said sample loading channel at a point between said first intersection and a point at which either of said at least two sample sources are in fluid communication with said sample loading channel.

6. The microfluidic system of claim 1, wherein said plurality of sample sources comprises at least four separate sample sources.

7. The microfluidic system of claim 6, wherein at least two separate sample sources are in fluid communication with said sample loading channel on each side of said first intersection.

8. The microfluidic system of claim 1, wherein said analysis channel comprises a buffer reservoir in fluid communication with a first terminus of said analysis channel, first and second waste reservoirs disposed at termini of the first and second load/waste channels, respectively, and a third waste reservoir in fluid communication with a second terminus of said analysis channel.

9. The microfluidic system of claim 1, wherein said substrate comprises silica.

10. The microfluidic system of claim 1, wherein said substrate comprises:
- a first planar member having a first surface, wherein each of said analysis channel, sample loading channel and first and second load waste channels comprise grooves disposed in said first surface; and
- a second planar member overlaying and sealably covering said first surface.

11. The microfluidic system of claim 10, wherein each of said plurality of sample sources comprises a separate hole disposed through said second planar member, and in fluid communication with a separate sample channel when said second planar member is overlaying said first planar member, said separate sample channel being in fluid communication with said sample loading channel.

12. The microfluidic system of claim 1, wherein each of said separate sample sources comprises a sample fluid reservoir disposed in said substrate and in fluid communication with said sample loading channel.

13. The microfluidic system of claim 1, wherein said analysis channel comprises a separation medium disposed therein.

14. A microfluidic system, comprising:
- a planar substrate having a first surface;
- an analysis channel disposed in said substrate;
- a sample loading channel disposed in said substrate and in fluid communication and crossing said analysis channel at a first intersection;
- at least six separate sample sources in fluid communication with said sample loading channel, whereby there is at least one of said at least six sample sources in fluid communication with said sample loading channel on each side of said first intersection; and
- first and second load/waste channels disposed in said substrate, each of said first and second load/waste channels intersecting said sample loading channel at second and third intersections, respectively, said second and third intersections being on different sides of said first intersection.

15. The microfluidic system of claim 14, wherein at least three separate sample sources are in fluid communication with said sample loading channel on each side of said first intersection.

16. The microfluidic system of claim 14, comprising at least eight separate sample sources.

17. The microfluidic system of claim 16, wherein at least four separate sample sources are in fluid communication with said sample loading channel on each side of said first intersection.

18. A microfluidic system, comprising:
- a planar substrate having a first surface;
- an analysis channel disposed in said substrate;
- a sample loading channel disposed in said substrate and in fluid communication and crossing said analysis channel at a first intersection;
- a plurality of separate sample fluid reservoirs disposed in said substrate and in fluid communication with said sample loading channel, whereby there is at least one of said plurality of sample sources in fluid communication with said sample loading channel on each side of said first intersection, and wherein a distance from each of said sample fluid reservoirs to said first intersection via said loading channel is less than two centimeters; and
- first and second load/waste channels disposed in said substrate, each of said first and second load/waste channels intersecting said sample loading channel at second and third intersections, respectively, said second and third intersections being on different sides of said first intersection.

19. The microfluidic system of claim 18, wherein a distance from each of said plurality of sample fluid reservoirs to said first intersection via said loading channel is less than one centimeter.

20. A microfluidic system, comprising:
- a planar substrate having a first surface;
- an analysis channel disposed in said substrate;
- a sample loading channel disposed in said substrate and in fluid communication and crossing said analysis channel at a first intersection;
- a plurality of separate sample sources in fluid communication with said sample loading channel, whereby there is at least one of said plurality of sample sources in fluid communication with said sample loading channel on each side of said first intersection; and
- first and second load/waste channels disposed in said substrate, each of said first and second load/waste channels intersecting said sample loading channel at second and third intersections, respectively, said second and third intersections being on different sides of said first intersection;
- wherein said analysis channel comprises a buffer reservoir in fluid communication with a first terminus of said analysis channel, first and second waste reservoirs disposed at termini of the first and second load/waste channels, respectively, and a third waste reservoir in fluid communication with a second terminus of said analysis channel; and
- a material direction system for transporting a sample material from each of said plurality of sample through said sample loading channel and into one of said first and second waste reservoirs.

21. The microfluidic system of claim 20, wherein said material direction system comprises:
- a different electrode placed in electrical contact with each of said plurality of different sample sources, said first, second and third waste reservoirs and said buffer reservoir; and
- a voltage source for applying a voltage at each of said different electrodes.

22. A microfluidic system, comprising:
- a planar substrate;
- an analysis channel disposed in said substrate;
- a sample loading channel disposed in said substrate and in fluid communication and crossing said analysis channel at a first intersection;
- a plurality of separate sample sources in fluid communication with said sample loading channel, whereby there is at least one of said plurality of sample sources in fluid communication with said sample loading channel on each side of said first intersection; and
- first and second load/waste channels disposed in said substrate, each of said first and second load/waste channels intersecting said sample loading channel at second and third intersections, respectively, said second and third intersections being on different sides of said first intersection; and a material direction system for transporting sample material from each of said plurality of sample sources and injecting at least a portion of said sample material into said analysis channel.

23. The microfluidic system of claim 22, wherein the substrate comprises silica.

24. The microfluidic system of claim 22, wherein the substrate comprises a polymer.

25. The microfluidic system of claim 24, wherein the substrate comprises a polymer selected from polydimethylsiloxane, polymethylmethacrylate, polyurethane, polyvinylchloride, polystyrene, polysulfone, and polycarbonate.

26. The microfluidic system of claim 25, wherein the substrate comprises polymethylmethacrylate.

27. The microfluidic system of claim 22, wherein the analysis channel comprises a sieving matrix disposed therein.

28. The microfluidic system of claim 27, wherein the sieving matrix comprises a linear polyacrylamide polymer.

29. The microfluidic system of claim 28, wherein the linear polyacrylamide polymer comprises a charged polymer.

30. The microfluidic system of claim 22, wherein the plurality of sample sources comprises a plurality of separate sample fluid reservoirs disposed in the substrate.

31. The microfluidic system of claim 22, wherein each of the analysis channel, sample loading channel and load/waste channels comprises at least one cross-sectional dimension between about 1 and 100 $\mu$m.

32. The microfluidic system of claim 22, wherein the plurality of sample sources comprises at least four separate sample sources.

33. The microfluidic system of claim 22, wherein the plurality of sample sources comprises at least eight separate sample sources.

34. A microfluidic system, comprising:
a planar substrate having a first surface;
an analysis channel disposed in said substrate;
a sample loading channel disposed in said surface on a first side of said analysis channel, and intersecting said analysis channel at a first intersection;
a plurality of sample reservoirs in fluid communication with said sample loading channel on said first side of said analysis channel;
a waste channel disposed in said substrate on a second side of said analysis channel, and intersecting said analysis channel at a second intersection; and
a waste reservoir in fluid communication with said waste channel on said second side of said analysis channel; and
wherein said plurality of sample reservoirs comprises at least four separate sample reservoirs.

35. The microfluidic system of claim 34, wherein said plurality of sample sources comprises at least six separate sample reservoirs.

36. The microfluidic system of claim 34, wherein said plurality of sample sources comprises at least eight separate sample reservoirs.

37. The microfluidic system of claim 34, wherein the substrate comprises silica.

38. The microfluidic system of claim 34, wherein the substrate comprises a polymer.

39. The microfluidic system of claim 38, wherein the substrate comprises a polymer selected from polydimethylsiloxane, polymethylmethacrylate, polyurethane, polyvinylchloride, polystyrene, polysulfone, and polycarbonate.

40. The microfluidic system of claim 39, wherein the substrate comprises polymethylmethacrylate.

41. The microfluidic system of claim 34, wherein the analysis channel comprises a sieving matrix disposed therein.

42. The microfluidic system of claim 41, wherein the sieving matrix comprises a linear polyacrylamide polymer.

43. The microfluidic system of claim 42, wherein the linear polyacrylamide polymer comprises a charged polymer.

44. The microfluidic system of claim 34, wherein each of the analysis channel, sample loading channel and load/waste channels comprises at least one cross-sectional dimension between about 1 and 100 $\mu$m.

45. The microfluidic system of claim 34, wherein the plurality of sample reservoirs comprises at least eight separate sample reservoirs.

46. A microfluidic system, comprising:
a planar substrate having a first surface;
an analysis channel disposed in said substrate;
first and second transverse channels, said first transverse channel being disposed in said substrate on a first side of said analysis channel, and intersecting said analysis channel at a first intersection, and said second transverse channel being disposed in said substrate on a second side of said analysis channel, and intersecting said analysis channel at a second intersection;
a first sample source in fluid communication with said first transverse channel;
at least a second sample source in fluid communication with said second transverse channel;
a first waste channel intersecting said first transverse channel at a third intersection;
at least a second waste channel intersecting said second transverse channel at a fourth intersection; and
a material direction system for individually transporting a sample from each of said first and second sample sources to said first and second waste channels via said first and second transverse channels, respectively, and selectively injecting said samples into said analysis channel.

47. The microfluidic system of claim 46, wherein said first and second intersections are located at the same point along said analysis channel.

48. The microfluidic system of claim 46, wherein the substrate comprises silica.

49. The microfluidic system of claim 46, wherein the substrate comprises a polymer.

50. The microfluidic system of claim 49, wherein the substrate comprises a polymer selected from polydimethylsiloxane, polymethylmethacrylate, polyurethane, polyvinylchloride, polystyrene, polysulfone, and polycarbonate.

51. The microfluidic system of claim 50, wherein the substrate comprises polymethylmethacrylate.

52. The microfluidic system of claim 46, wherein the analysis channel comprises a sieving matrix disposed therein.

53. The microfluidic system of claim 52, wherein the sieving matrix comprises a linear polyacrylamide polymer.

54. The microfluidic system of claim 53, wherein the linear polyacrylamide polymer comprises a charged polymer.

55. The microfluidic system of claim 46, further comprising at least a third sample source in fluid communication with the first transverse channel.

56. The microfluidic system of claim 55, further comprising at least a fourth sample source in fluid communication with the second transverse channel.

57. The microfluidic system of claim 56, wherein each of the analysis channel, first and second transverse channels comprises at least one cross-sectional dimension between about 1 and 100 $\mu$m.

58. A microfluidic system, comprising:
a planar substrate having a first surface;
an analysis channel disposed in said substrate;
first and second transverse channels, said first transverse channel being disposed in said substrate on a first side of said analysis channel, and intersecting said analysis channel at a first intersection, and said second transverse channel being disposed in said surface on a second side of said analysis channel, and intersecting said analysis channel at a second intersection;
a plurality of sample sources in fluid communication with said first transverse channel;
a first waste channel intersecting said first transverse channel at a third intersection;
at least a second waste channel intersecting said second transverse channel at a fourth intersection; and
a material direction system for individually transporting a sample from each of said plurality of sample sources to said first and second waste channels via said first and second transverse channels, respectively, and selectively injecting said samples into said analysis channel.

59. The microfluidic system of claim 58, wherein said first and second intersections are located at the same point along said analysis channel.

60. The microfluidic system of claim 58, wherein the substrate comprises silica.

61. The microfluidic system of claim 58, wherein the substrate comprises a polymer.

62. The microfluidic system of claim 61, wherein the substrate comprises a polymer selected from polydimethylsiloxane, polymethylmethacrylate, polyurethane, polyvinylchloride, polystyrene, polysulfone, and polycarbonate.

63. The microfluidic system of claim 62, wherein the substrate comprises polymethylmethacrylate.

64. The microfluidic system of claim 58, wherein the analysis channel comprises a sieving matrix disposed therein.

65. The microfluidic system of claim 64, wherein the sieving matrix comprises a linear polyacrylamide polymer.

66. The microfluidic system of claim 65, wherein the linear polyacrylamide polymer comprises a charged polymer.

67. The microfluidic system of claim 58, wherein the plurality of sample sources in fluid communication with the first transverse channel comprises at least four separate sample sources.

68. The microfluidic system of claim 58, wherein the plurality of sample sources in fluid communication with the first transverse channel comprises at least six separate sample sources.

69. The microfluidic system of claim 66, wherein each of the analysis channel, first and second transverse channels comprises at least one cross-sectional dimension between about 1 and 100 $\mu$m.

70. A method of analyzing a plurality of different sample materials, comprising:
providing a microfluidic device which comprises:
a planar substrate having a first surface;
an analysis channel disposed in said substrate;
a sample loading channel disposed in said substrate and intersecting said analysis channel at a first intersection, wherein said sample loading channel crosses said analysis channel; and
at least first and second sample sources in fluid communication with said sample loading channel;
a waste reservoir in fluid communication on a same side of said first intersection as said second sample source;
transporting a first sample from a first of said plurality of sample sources, through said sample loading channel to said first intersection;
injecting a portion of said first sample into said analysis channel;
analyzing said first sample in said analysis channel;
transporting said second sample through said sample loading channel and into said waste reservoir; and
injecting a portion of said second sample into said analysis channel.

71. The method of claim 70, wherein said step of transporting said second sample through said sample loading channel and into said waste reservoir is carried out substantially concurrently with said step of analyzing said first sample.

72. The method of claim 70, wherein each of said first and second samples comprises a plurality of nucleic acid fragments and said analysis channel comprises a sieving matrix.

73. The method of claim 70, wherein the step of transporting the first sample comprises electrokinetically transporting the first sample from the first sample source, through the sample loading channel to the intersection.

74. The method of claim 70, wherein the step of analyzing the first sample comprises separating the first sample into constituent elements and detecting the constituent elements.

75. The method of claim 74, wherein the first sample comprises proteins.

76. A method of performing analysis on a plurality of different sample materials, comprising:
providing a microfluidic device which comprises:
a planar substrate having a first surface;
an analysis channel disposed in said substrate;
a sample loading channel disposed in said substrate and intersecting said analysis channel at a first intersection; and
a sample preloading module which comprises at least first and second sample reservoirs and a waste reservoir, wherein each of said plurality of sample reservoirs and said waste reservoir are in fluid communication with said sample loading channel;
transporting a first sample from said first sample reservoir to said first intersection;
injecting a portion of said first sample into said analysis channel;
concurrently analyzing said portion of said first sample in said analysis channel and transporting a second sample from said second sample reservoir into said loading channel and then to said waste reservoir;
transporting said second sample from said loading channel to said intersection;
injecting a portion of said second sample into said analysis channel; and
analyzing said portion of said second sample in said analysis channel.

77. The method of claim 76, wherein the step of transporting the first sample comprises electrokinetically transporting the first sample from the first sample source, through the sample loading channel to the intersection.

78. The method of claim 76, wherein the step of analyzing the first sample comprises separating the first sample into constituent elements and detecting the constituent elements.

79. The method of claim 78, wherein the first sample comprises proteins.

80. The method of claim 76, wherein the sample preloading module further comprises at least a third sample reservoir in fluid communication with the sample loading channel, and further comprising the step of transporting a third sample from said third sample reservoir into said loading channel and then to said waste reservoir, concurrently with the step of analyzing said portion of said second sample in said analysis channel.

81. The method of claim 80, wherein the sample preloading module further comprises at least a fourth sample reservoir in fluid communication with the sample loading channel, and further comprising:

injecting a portion of the third sample into said analysis channel;

analyzing the portion of the third sample in the analysis channel; and transporting a fourth sample from said fourth sample reservoir into said loading channel and then to said waste reservoir, concurrently with the step of analyzing said portion of said third sample in said analysis channel.

\* \* \* \* \*

UNITED STATES PATENT AND TRADEMARK OFFICE
CERTIFICATE OF CORRECTION

PATENT NO: 5,976,336
DATED:      November 2, 1999
INVENTOR(S):    Dubrow et al.

It is certified that error appears in the above-identified patent and that said Letters Patent are hereby corrected as shown below:

Column 16, line 42, after "sample", please insert --sources--.

Column 19, line 62, please delete "66" and insert --68--.

Signed and Sealed this

Third Day of April, 2001

*Attest:*

NICHOLAS P. GODICI

*Attesting Officer*    *Acting Director of the United States Patent and Trademark Office*